United States Patent
Chng et al.

(10) Patent No.: US 7,062,012 B1
(45) Date of Patent: Jun. 13, 2006

(54) LEAK DETECTION OF SEALED OBJECTS USING X-RAY IMAGING

(75) Inventors: Kiong Chin Chng, Singapore (SG); Cheng Yun Audrey Wong, Singapore (SG)

(73) Assignee: Hewlett-Packard Development Company, L.P., Houston, TX (US)

( * ) Notice: Subject to any disclaimer, the term of this patent is extended or adjusted under 35 U.S.C. 154(b) by 55 days.

(21) Appl. No.: 11/009,240

(22) Filed: Dec. 9, 2004

(51) Int. Cl.
*G01N 23/04* (2006.01)
*G01N 23/00* (2006.01)
*G01N 23/201* (2006.01)

(52) U.S. Cl. .................... 378/57; 378/19; 378/88
(58) Field of Classification Search .......... 378/4, 378/16, 19, 45, 50, 57, 59, 62, 80–83; 73/40, 73/40.7
See application file for complete search history.

(56) References Cited

U.S. PATENT DOCUMENTS

| | | | | |
|---|---|---|---|---|
| 3,487,677 A | * | 1/1970 | Molitor | 73/40.7 |
| 3,762,212 A | | 10/1973 | Morley et al. | |
| 4,267,449 A | * | 5/1981 | DeLuca et al. | 250/303 |
| 4,772,789 A | * | 9/1988 | Maram et al. | 250/330 |
| 4,779,621 A | * | 10/1988 | Mattson | 600/431 |
| 5,008,540 A | * | 4/1991 | Dempsey | 250/336.1 |
| 5,126,567 A | * | 6/1992 | Dempsey et al. | 250/336.1 |
| 5,361,626 A | * | 11/1994 | Colligan et al. | 73/40.7 |
| 5,458,111 A | * | 10/1995 | Coin | 600/560 |
| 5,572,327 A | | 11/1996 | Plinke et al. | |
| 6,337,895 B1 | * | 1/2002 | Sase | 378/8 |

FOREIGN PATENT DOCUMENTS

GB 1109673 A 4/1968

OTHER PUBLICATIONS

International Search Report for Application No. PCT/US2005/038405 based on U.S. Appl. No. 11/009,240; report issued Feb. 8, 2006.

* cited by examiner

*Primary Examiner*—Edward J. Glick
*Assistant Examiner*—Irakli Kiknadze
(74) *Attorney, Agent, or Firm*—Jeff D. Limon

(57) ABSTRACT

A method of detecting a leak in a sealed object includes placing the sealed object into a chamber and introducing an x-ray attenuating gas into the chamber. The method also includes observing, by way of x-ray imaging, the transfer of the x-ray attenuating gas between the sealed object and the chamber.

32 Claims, 6 Drawing Sheets

LEAK DETECTION OF SEALED OBJECTS USING X-RAY IMAGING

BACKGROUND OF THE INVENTION

Many electronic tube devices are hermetically sealed to protect delicate internal components from corrosion and other environmental effects that reduce the life of the tube and degrade its performance. However, it can often be difficult to detect small leaks in a hermetic seal, allowing defective electronic tube devices to be incorporated into larger electronic systems and sold to a customer. Over time, as more and more of the outside environment leaks into the tube device causing the tube to degrade, the performance of the larger system degrades.

Existing techniques for determining leaks in a hermetic seal include the use of a radioactive tracer gas that is used to fill a test chamber. The electronic tube device is then placed within the chamber allowing the tracer gas to enter the device. The device is then removed from the chamber and tested for the presence of the radioactive tracer gas. However, this can require the destruction of the electronic tube device, thus rendering the method unsuitable for 100 percent sampling. Further, the use of a radioactive gas also raises environmental health and safety concerns.

DESCRIPTION OF THE EMBODIMENTS

Leak detection of sealed objects using x-ray imaging provides a nondestructive technique for determining the presence of a leak in a hermetically sealed object as well as determining the precise location of the leak. The technique does not require the use of radioactive gases, and is suitable for 100 percent sampling. The technique can be used to detect the influx of x-ray-absorbing gas from the test chamber into the sealed object, or the outflow of x-ray-absorbing gas from the sealed object into the test chamber.

Figure 1:
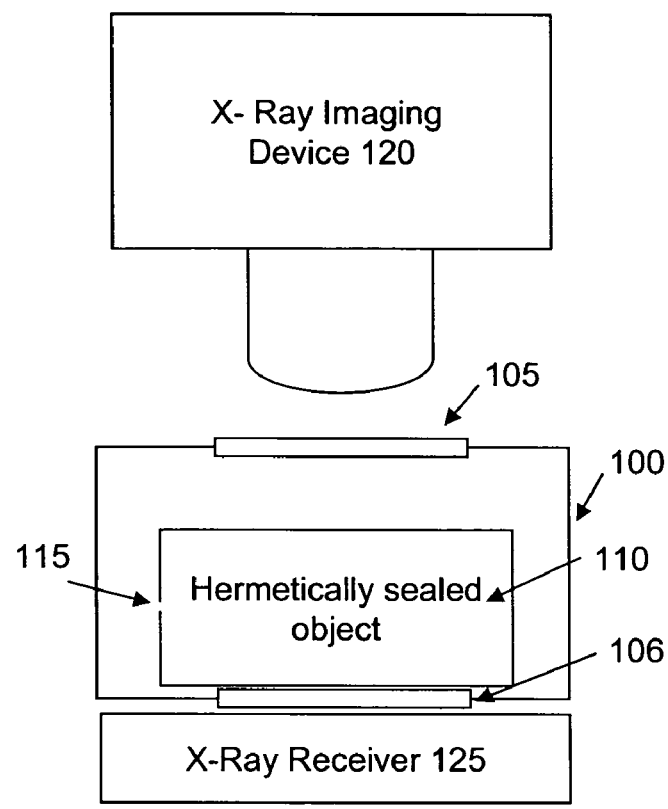
FIG. 1 is a diagram that shows the environment in which an embodiment of the invention may be practiced.

FIG. 1 is a diagram that shows the environment in which an embodiment of the invention may be practiced. In FIG. 1, hermetically sealed object 110 is placed within chamber 100. Chamber 100 is then filled with an inert x-ray attenuating gas, such as helium, neon, argon, krypton, xenon, or radon. Over time, the inert gas from chamber 100 leaks into hermetically sealed object 110. At an appropriate time, an x-ray imaging device 120 transmits a beam of x-rays through x-ray transparent window 105, through hermetically sealed object 110, and through x-ray transparent window 106. The attenuated beam is then received by x-ray receiver 125.

In the embodiment of FIG. 1, hermetically sealed object 110 may be filled with an x-ray attenuating gas prior to sealing and prior to the object being placed into chamber 100. In this event, chamber 100 may be closed and the ambient air pumped out of the chamber so that the air pressure in the chamber is much lower than the pressure of the gas within sealed object 110. In this event, the gas within the sealed object absorbs a decreasing amount of x-ray energy from imaging device 120 as the x-ray attenuating gas leaks from the sealed object. Further, x-ray imaging device 120 may be used either to determine the concentration of the x-ray attenuating gas remaining in hermetically sealed object 110 or may be used to determine the concentration of the x-ray attenuating gas present in chamber 100. Thus, either the object (110) or the chamber (100) may be imaged to determine the presence of the x-ray attenuating gas.

FIGS. 2a–2d are diagrams that illustrate a principle of leak detection of sealed objects using x-ray imaging according to an embodiment of the invention. In FIGS. 2a–2d, the shaded areas represent a hermetically sealed object and the chamber as viewed by an x-ray imaging device. For example, in FIG. 2a a hermetically sealed object (represented by shaded area 110A) has been placed into chamber 100A and viewed by way of an x-ray imaging device. Vacuum pump 150 has removed all or nearly all of the ambient air or other gas within chamber 100A. The shaded area 110A conforms to the volume that is enclosed by the hermetically sealed object. For the case of FIG. 2a, the hermetically sealed object may be filled with krypton or other inert or noble gas.

Figure 2A:
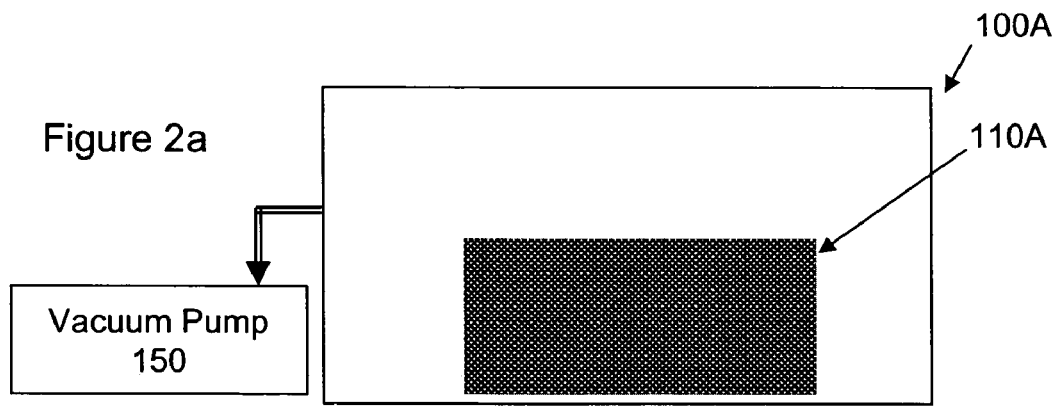
FIGS. 2a–2d are diagrams that illustrate a principal of leak detection of sealed objects using x-ray imaging according to an embodiment of the invention.
Figure 2B:
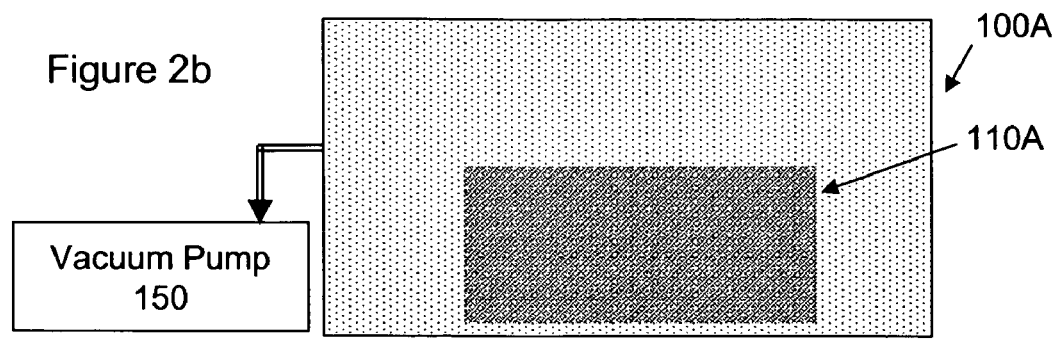

FIG. 2b represents chamber 100A as well as hermetically sealed object 110 as viewed by an x-ray imaging device after an appropriate period of time has elapsed. As indicated by shaded area 110A within chamber 100A, at least some of the krypton gas within the hermetically sealed object has leaked outside of the object and into chamber 100A. Thus, by way of an x-ray imaging device, the leakage of the x-ray attenuating gas from the object can be viewed within the chamber.

In another embodiment, hermetically sealed object 110 is removed from the chamber 100 and evaluated by way of x-ray imaging. As a result of the leakage of the x-ray attenuating gas from the sealed object into the vacuum chamber, the change in the contrast brought about by the leakage can be used to detect the amount of x-ray attenuating gas that remains in the object.

Figure 2C:
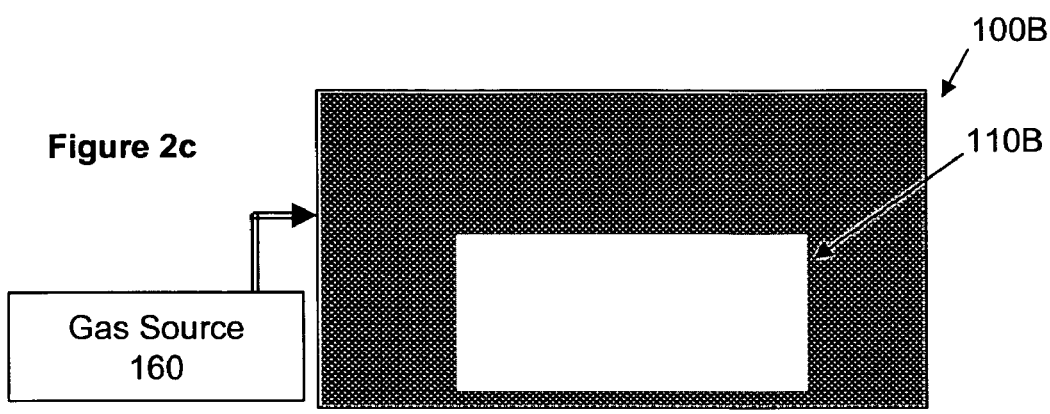

In FIG. 2c, a hermetically sealed object (represented by unshaded area 110A) has been placed within chamber 10B. As indicated by unshaded area 110B, there is little or no x-ray attenuating gas within the hermetically sealed object. Gas source 160 is used to pump an x-ray attenuating gas into chamber 100B. In the embodiment of FIG. 2c, the x-ray attenuating gas present in chamber 100B is maintained at a higher pressure relative to the pressure within the hermetically sealed object represented by unshaded area 110B. In some embodiments, the interior of the hermetically sealed object may be maintained at a vacuum.

Figure 2D:
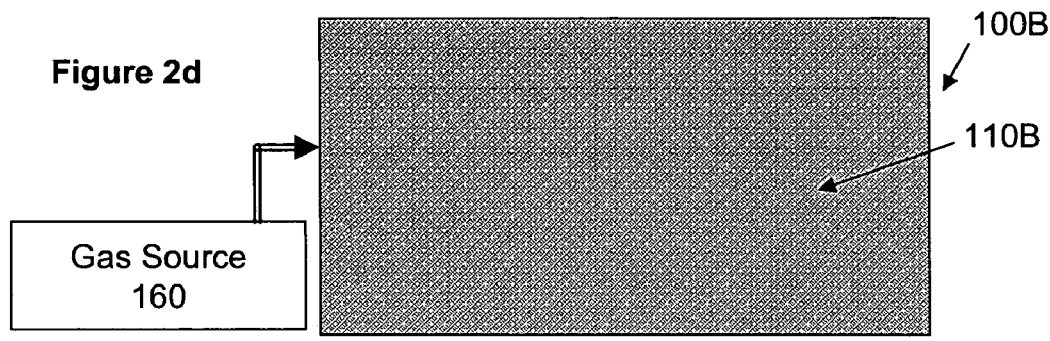

FIG. 2d represents chamber 100B after an appropriate length of time, such as an hour or more, has elapsed. As seen by the uniformly shaded area within chamber 100B as well as within the hermetically sealed object represented by unshaded area 110B, at least some of the x-ray attenuating gas from chamber 100B has leaked into the hermetically sealed object. Thus, an x-ray beam passing through the hermetically sealed object represented by shaded area 110B can be used to detect an increasing amount of x-ray attenuating gas leaking into the hermetically sealed object. In another embodiment, an x-ray beam passing through chamber 100B at a location outside of the hermetically sealed object can be used to detect a decreasing amount of x-ray attenuating gas in chamber 100B and an increasing amount of x-ray attenuating gas present in the hermetically sealed object as the gas leaks into the object.

Figure 3A:
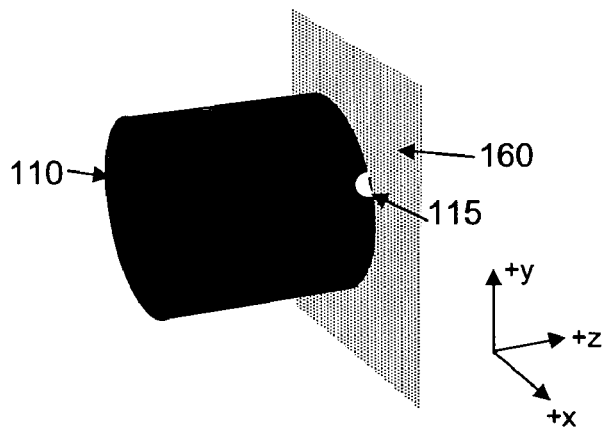
FIGS. 3a–3b are front and side views of a sealed object undergoing imaging of by way of computer aided x-ray tomography according to an embodiment of the invention.
Figure 3B:
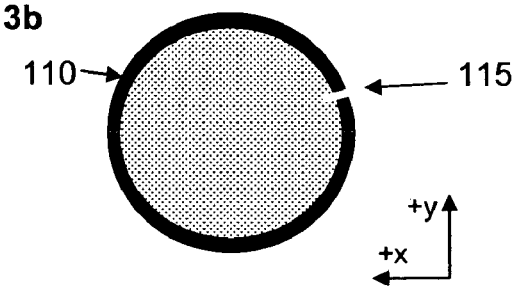

FIGS. 3a–3b are a front and side view of a sealed object undergoing imaging of by way of computer aided x-ray tomography according to an embodiment of the invention. In FIG. 3a, hermetically sealed object 110 is undergoing computer aided x-ray tomography. As the tomographic x-ray imaging device scans hermetically sealed object 110 along the length of the object (in the +z direction) imaging information in the form of "slices" result from the imaging process. In FIG. 3a, slice 160 has identified hole 115 in hermetically sealed object 110. Using conventional computer aided x-ray tomography, it is contemplated that hole 115 may be on the order of 10 microns or less. However, nothing prevents the use of computer aided tomography equipment having much higher resolution and thus being capable of detecting a hole having a diameter of one micron or less. Further, nothing prevents the use of imaging equipment having much lower resolution, such as 100 microns or more.

In FIG. 3b, slice 160 is shown in the x-y plane. As shown by the shaded area within hermetically sealed object 110, hole 115 can be detected by way of the presence of x-ray attenuating gas present in the hole as the attenuating gas enters or exits sealed object 110.

Figure 4:
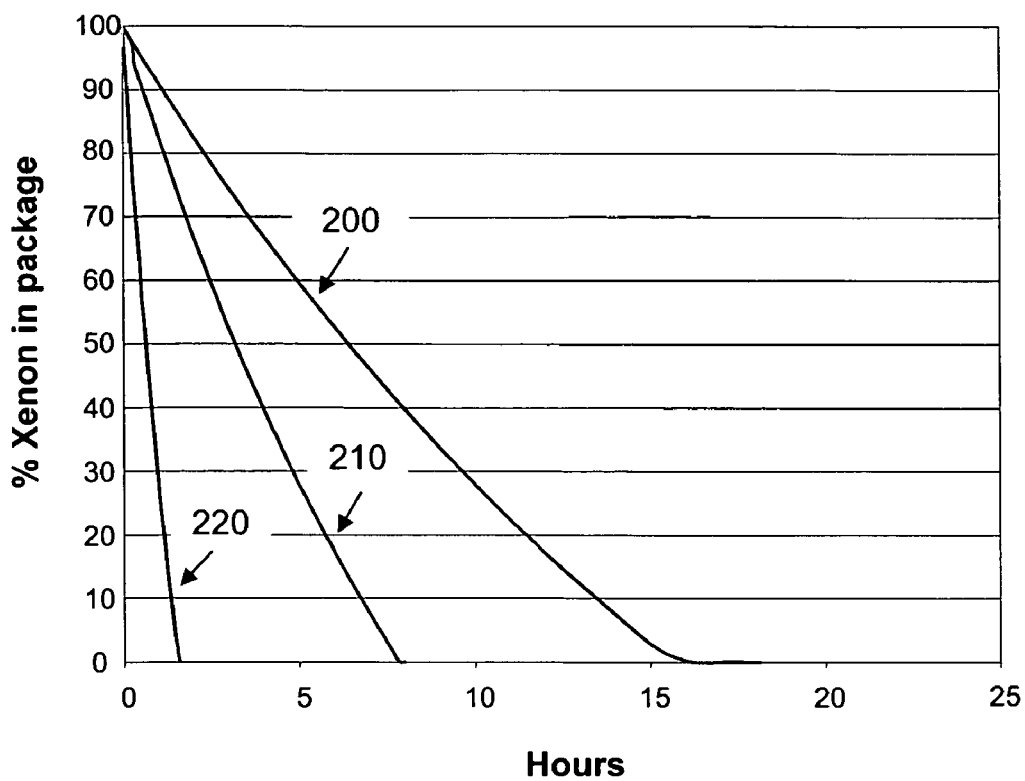
FIG. 4 is a graph showing leakage rate as a function of time for various sizes of sealed object volume and for a leakage rate of $10^{-4}$ Pa L/Sec according to an embodiment of the invention.

FIG. 4 is a graph showing the leakage rate of xenon gas as a function of time for various sizes of sealed object volume and for a leakage rate of $10^{-4}$ Pa L/Sec, according to an embodiment of the invention. In FIG. 4, curve 200 shows leakage from a sealed container having a volume of 0.01 cc. Curve 200 shows that after approximately 15 hours, nearly all of the xenon within the volume has leaked from the container. Curve 210 of FIG. 4 shows leakage from a sealed container having a volume of 0.005 cc. Curve 210 shows that after approximately eight hours, nearly all of the xenon within the 0.005 cc volume has leaked from the container. Curve 220 of FIG. 4 shows leakage from a sealed container having a volume of 0.001 cc. Curve 220 shows that after approximately one hour, nearly all of the xenon within the 0.001 cc volume has leaked from the container. Thus, curves 200, 210, and 220 show that for a constant leakage rate, sealed containers having a smaller volume exhibit a faster rate of leakage of the x-ray attenuating gas within the container when compared to larger containers. FIG. 4 can thus be used as a guideline in determining the amount of x-ray attenuating gas present in a given size container as a function of time.

Figure 5:
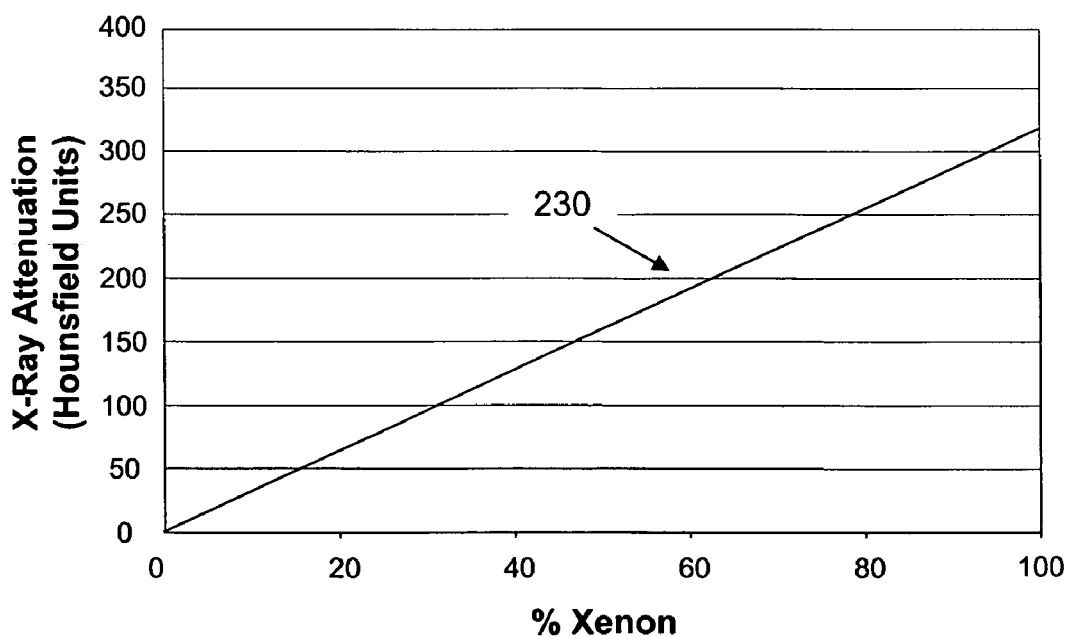
FIG. 5 is a graph showing x-ray attenuation as a function of a percentage of xenon gas present in a sealed object according to an embodiment of the invention.

FIG. 5 is a graph showing x-ray attenuation as a function of the percentage of xenon gas present in a sealed object according to an embodiment of the invention. The vertical axis of FIG. 5 provides an indication of x-ray attenuation as manifested in Hounsfield units. In the context of the present invention, a Hounsfield unit is a unit for reporting and displaying reconstructed x-ray computed tomography values. In FIG. 5, curve 230 represents the relationship of Hounsfield units versus the percentage of xenon within a container for an x-ray imaging device having an anode-to-cathode voltage of 40 kilovolts. From FIG. 5, the percentage of the x-ray attenuating gas remaining in the sealed object can be determined from the Hounsfield units reported by the x-ray imaging device.

Figure 6:
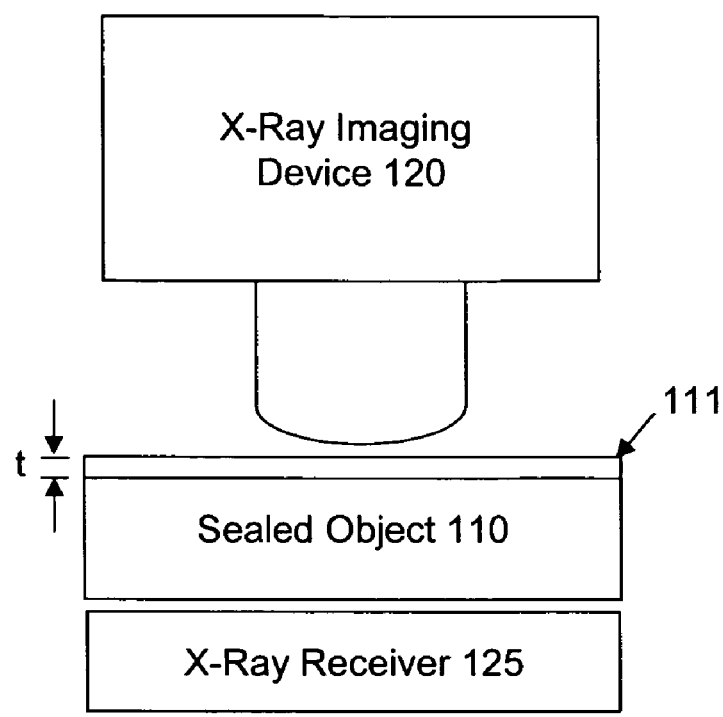
FIG. 6 is a diagram of a sealed object that includes a substrate according to an embodiment of the invention.

FIG. 6 is a diagram of a sealed object that includes a substrate according to an embodiment of the invention. In FIG. 6, substrate 111 represents the glass or other material that encases the components within the hermetically sealed device. The equation that governs the attenuation of x-rays through a material (including x-ray attenuating gas and glass or other material from which the case of the hermetically sealed device is constructed) is:

$$I_x = I_0 e^{[-(\mu/\rho)x]}$$

Wherein $I_0$ equals the initial x-ray beam intensity before passing through a material, $I_x$ equals the intensity of x-ray radiation after passing through a material, $\mu/\rho$ equals the mass attenuation coefficient, and wherein x equals the material thickness (t) multiplied by the density of the mass. From the above the equation, an x-ray transfer function $I_x/I_0$ can be expressed as $e^{[-(\mu/\rho)x]}$.

The mass attenuation coefficient, $\mu/\rho$ is contemplated as being dependent on the atomic mass of the element wherein the higher the atomic mass of the element, the higher the mass attenuation coefficient. The optical transfer function, $e^{[-(\mu/\rho)x]}$, thus depends on the density and the mass attenuation coefficient of the material. The optical transfer function can be visualized as being proportional to the inverse of the attenuation of a material (i.e. high attenuation implies low transfer function).

Figure 7A:
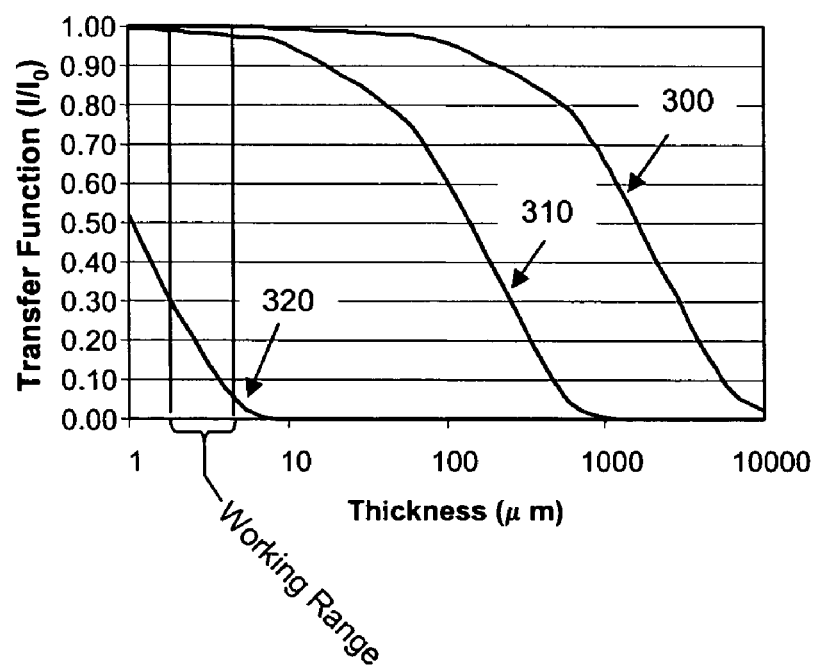
FIGS. 7a–7c show transfer functions for various materials using the x-ray source of FIG. 6 operated at a 1 kilovolt, 10 kilovolt, and 20 kilovolt anode-to-cathode voltage.
Figure 7B:
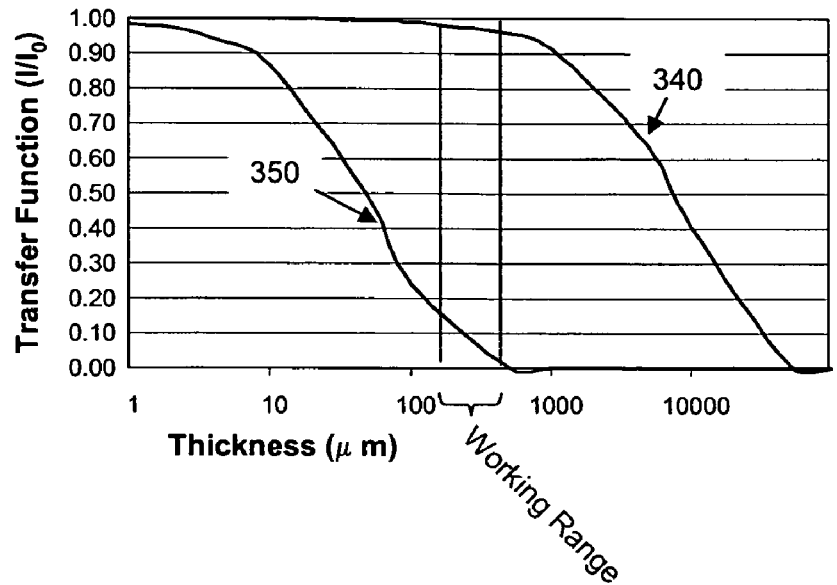
Figure 7C:
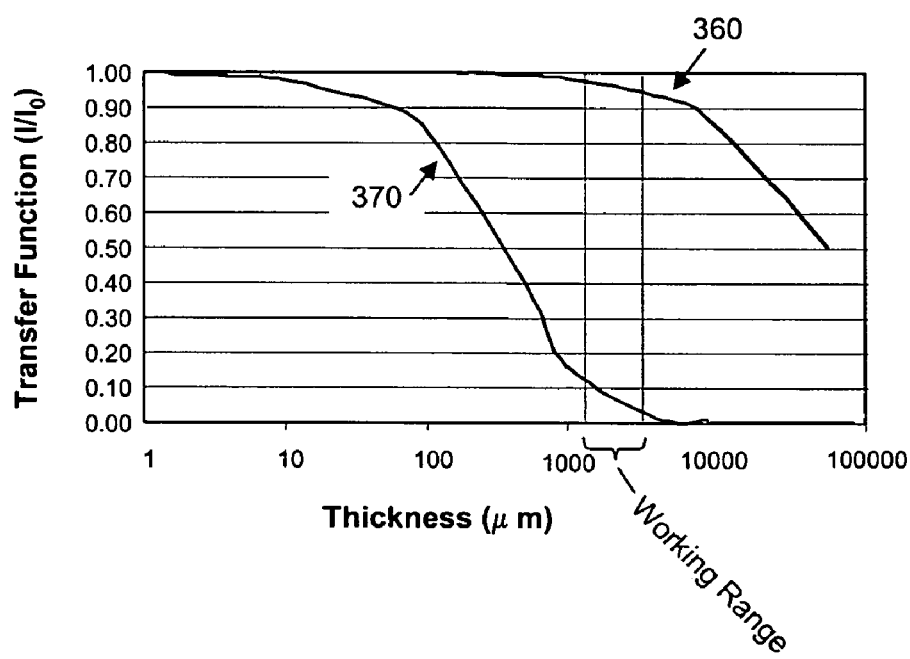

FIGS. 7a–7c show transfer functions for various materials using the x-ray source of FIG. 6 operated at a 1 kilovolt, 10 kilovolt, and 20 kilovolt anode-to-cathode voltage. FIG. 7a shows the transfer function of x-ray source 120 as seen by x-ray receiver 125 for an anode-to-cathode voltage of 1 kilovolt. In FIG. 7a it can be seen that curve 300, which represents dry air, attenuates x-rays by only a small amount. Curve 310, which represents xenon gas, attenuates x-rays by a larger extent. In the left corner of FIG. 7a (curve 320), silicon is shown as being a substantial attenuator of x-ray energy. Thus, from FIG. 7a, it can be seen that to determine the attenuation brought about by an x-ray attenuating gas, a silicon substrate of only three to five microns should be used. If substrate 111 is of a thickness on the order of 100 microns, for example, substrate 111 will appear to be completely opaque when viewed at x-ray receiver 125. This would prevent small changes in the concentration of xenon from being detected at x-ray receiver 125.

FIG. 7b shows the transfer function of an x-ray source (120) as seen by x-ray receiver 125 for an anode-to-cathode voltage of 10 kilovolts. FIG. 7b shows that a substrate thickness on the order of between 200 and 600 microns could be used before the substrate obscures the changes in x-ray attenuation brought about by varying changes in the concentration of xenon gas present in the object. In FIG. 7b it can be seen that at 10 kilovolts, xenon gas is largely transparent for thickness values of under 1 thousand microns.

Although FIG. 7b shows a combined working range of between 200 and 600 microns, this combined range can be optimized to reduce the thickness of substrate 111 (as represented by curve 350) and to increase the thickness of the xenon gas (as represented by curve 340) within the respective working range of each when each is allowed to vary independently. Thus, when combined, and depending on the sensitivity and contrast capabilities of the x-ray imaging device, the working range of the combination of silicon and xenon may be expanded to include substrate thicknesses as low as 10 microns and xenon thicknesses of as much as 104 micron.

FIG. 7c shows the transfer function of an x-ray source 120 as seen by x-ray receiver 125 for an anode-to-cathode voltage of 20 kilovolts. FIG. 7c shows that a substrate thickness on the order of between 1500 and 5000 microns could be used before the silicon substrate obscures the changes in x-ray attenuation brought about by varying changes in the concentration of xenon gas present in the object (curve 360). In FIG. 7c it can be seen that at 10 kilovolts, xenon gas (curve 360) is largely transparent for thickness values of under 1000 microns.

Although FIG. 7c shows a combined working range of between 1500 and 5000 microns, the combined range can be optimized to reduce the thickness of substrate 111 (as represented by curve 370) and to increase the thickness of the xenon gas (as represented by curve 360) within the respective working range of each when each is allowed to vary independently. Thus, when combined, and depending on the sensitivity and contrast capabilities of the x-ray imaging device, the working range of the combination of silicon and xenon may be expanded to include substrate thicknesses as low as 10 microns.

Substrate materials other than silicon may be used so long as the material possesses a transfer function that is high enough so as not to obscure small changes in the concentration of the underlying x-ray attenuating gas. In the examples of FIGS. 7a–7c, the attenuation brought about by the use of a silicon substrate has been assumed. However, a more suitable substrate might be a substrate that possesses an x-ray attenuation factor that is more closely aligned with the transfer function of ambient air. This would enable the substrate to be relatively thick and perhaps more structurally sound than thinner substrates while still allowing small changes in the concentration of the x-ray attenuating gas to be determined by the x-ray imaging device.

Figure 8:
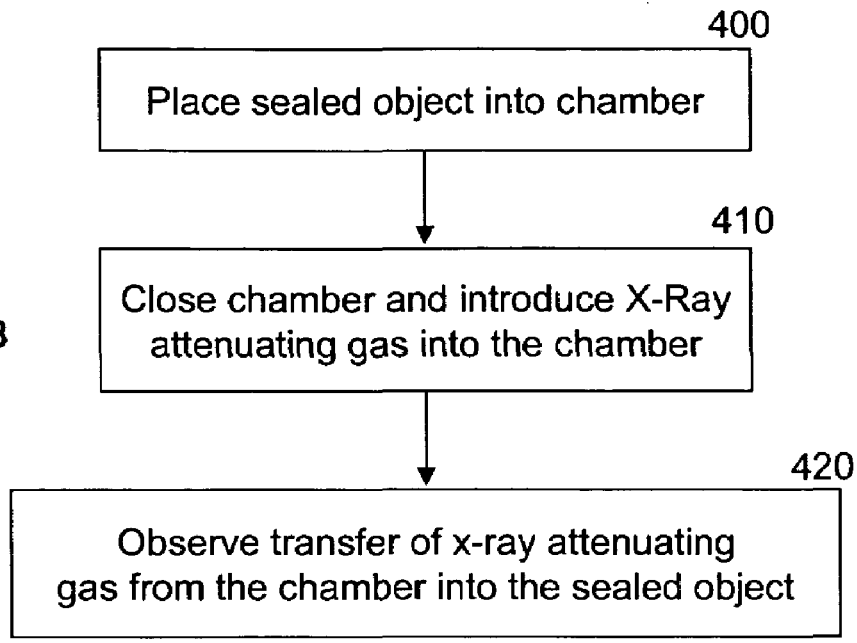
FIGS. 8 and 9 are flowcharts for methods of leak detection in sealed objects according to embodiments of the invention.

FIG. 8 is a flowchart for a method of detecting a leak in a sealed object according to an embodiment of the invention. The apparatus of FIG. 1 is suitable for performing the method of FIG. 8. In the method of FIG. 8, the sealed object is contemplated as having a low internal pressure, perhaps less than $10^4$ Pa. The method begins at step 400, in which a sealed object is placed into a chamber. At step 410, the chamber is closed and an x-ray attenuating gas is introduced into the chamber. In step 410, the x-ray attenuating gas is contemplated as being one of the group consisting of xenon, krypton, and radon. At step 420, the transfer of the x-ray attenuating gas from the chamber into the sealed object is observed by way of x-ray imaging. Step 420 may include the step of dividing the object into a plurality of planar slices and detecting an entrance of the x-ray attenuating gas in successive ones of the plurality of planar slices by way of computer-aided x-ray tomography. Step 420 may also include imaging the chamber to determine that an amount of the x-ray attenuating gas has left the chamber and leaked into the sealed object. In other embodiments, the observing step may include imaging the sealed object to determine that an amount of the x-ray attenuating gas has left the chamber and leaked into the sealed object.

In some embodiments, step 420 may be performed one hour after step 410. In other embodiments, step 420 may be performed less than an hour after step 410 or more than an hour after the completion of step 410.

Figure 9:
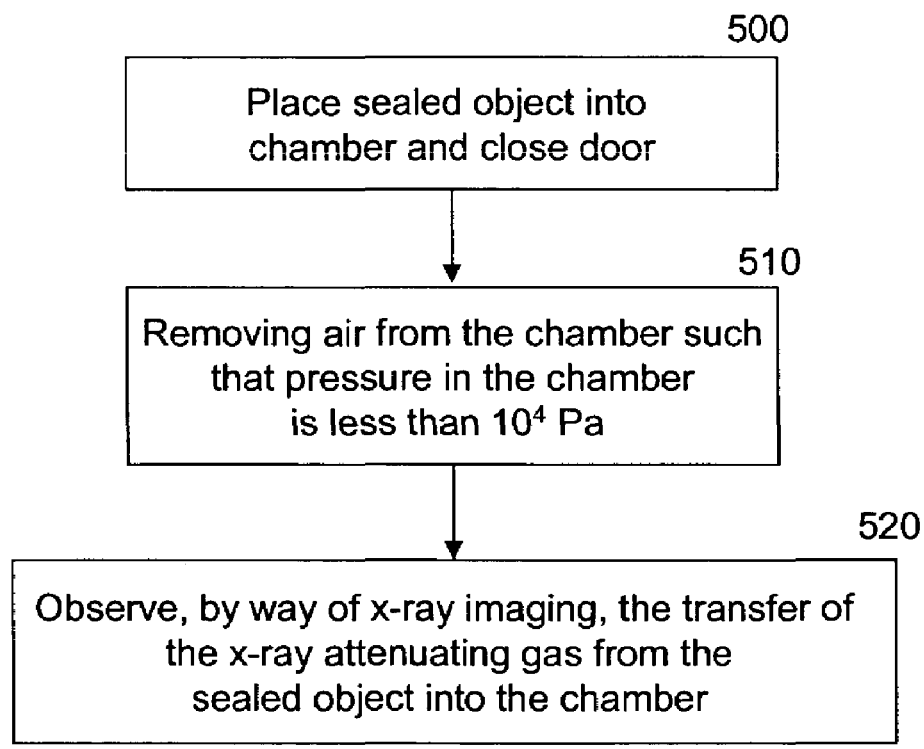

FIG. 9 is a flowchart for a second method of detecting a leak in a sealed object according to an embodiment of the invention. The apparatus of FIG. 1 is suitable for performing the method of FIG. 9. The method begins at step 500, in which the sealed object is placed into a chamber and the chamber is closed. In step 500, the sealed object is contemplated as being filled with an x-ray attenuating gas at a pressure that is between $5 \times 10^4$ and $1.5 \times 10^5$ Pa. The x-ray attenuating gas used in the method may be selected from the group consisting of xenon, krypton, and radon.

The method continues at step 510, which includes removing air from the chamber such that the pressure in the chamber is less than $10^4$ Pa. Step 520 includes observing, by way of x-ray imaging, the transfer of the x-ray attenuating gas from the sealed object into the chamber. Step 520 may further comprise dividing the object into a plurality of planar slices by way of computer-aided tomography and detecting a location on the object where the x-ray attenuating gas has leaked from by examining the plurality of planar slices. Further, step 520 may be performed one hour after placing the sealed object into the chamber. In other embodiments, step 520 may be performed less than an hour after step 510 or more than an hour after the completion of step 510.

In one embodiment, the observing step (520) may include testing the sealed object to determine that an amount of the x-ray attenuating gas has leaked from the sealed object into the chamber. In another embodiment, the observing step may include testing the chamber to determine the presence of x-ray attenuating gas in the chamber.

In conclusion, while the present invention has been particularly shown and described with reference to the foregoing embodiments, those skilled in the art will understand that many variations may be made therein without departing from the spirit and scope of the invention as defined in the following claims. This description of the invention should be understood to include the novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring nor excluding two or more such elements.

What is claimed is:

1. A method of detecting a leak in a sealed object, comprising:
    placing the sealed object into a chamber;
    introducing an x-ray attenuating gas into the chamber; and
    observing, by way of x-ray imaging, a transfer of the x-ray attenuating gas from the chamber into the sealed object.

2. The method of claim 1, wherein the x-ray attenuating gas is one of the group consisting of xenon, krypton, and radon.

3. The method of claim 1, wherein the observing step further comprises the step of dividing the sealed object into a plurality of planar slices by way of computer-aided x-ray tomography.

4. The method of claim 3, wherein the observing step further comprises detecting an entrance of the x-ray attenuating gas in successive ones of the plurality of planar slices.

5. The method of claim 1, wherein the observing step is performed at less than one hour after the introducing step.

6. The method of claim 1, further comprising increasing the pressure of the x-ray attenuating gas in the chamber relative to the pressure inside sealed object.

7. The method of claim 1, wherein the observing step includes imaging the chamber to determine that an amount of the x-ray attenuating gas has left the chamber and leaked into the sealed object.

8. The method of claim 1, wherein the observing step includes imaging the sealed object to determine that an amount of the x-ray attenuating gas has left the chamber and leaked into the sealed object.

9. The method of claim 1, wherein the sealed object is hermetically sealed.

10. A method of detecting a leak in a sealed object, comprising:
   placing the sealed object into a chamber, the sealed object being filled with an x-ray attenuating gas at a pressure that is between $5 \times 10^4$ Pa and $1.5 \times 10^5$ Pa;
   removing air from the chamber such that the pressure in the chamber is less than $10^4$ Pa; and
   observing, by way of x-ray imaging, a transfer of the x-ray attenuating gas from the sealed object into the chamber.

11. The method of claim 10, wherein the x-ray attenuating gas is selected from the group consisting of xenon, krypton, and radon.

12. The method of claim 10, wherein the observing step further comprises dividing the object into a plurality of planar slices by way of computer-aided tomography.

13. The method of claim 12, wherein the observing step further comprises detecting a location on the sealed object where the x-ray attenuating gas is leaking from by examining at least some of the plurality of planar slices.

14. The method of claim 10, wherein the observing step is performed less than one hour after placing the sealed object into the chamber.

15. The method of claim 10, wherein the observing step includes testing the sealed object to determine that an amount of the x-ray attenuating gas has leaked from the sealed object into the chamber.

16. The method of claim 10, further comprising removing the sealed object from the chamber prior to the observing step.

17. The method of claim 10, wherein the observing step includes testing the chamber to determine the presence of x-ray attenuating gas in the chamber.

18. A system for detecting a leak in a sealed object, comprising:
   a chamber, into which the sealed object can be placed;
   a vacuum pump that removes a substantial portion of ambient gas from the chamber while the sealed object is inside the chamber; and
   an x-ray imaging device that senses a transfer of the x-ray attenuating gas from the sealed object into the chamber.

19. The system of claim 18, wherein the x-ray imaging device senses the transfer of the x-ray attenuating gas from the sealed object into the chamber by comparing successive ones of a plurality of planar slices using computer-aided x-ray tomography.

20. The system of claim 18, wherein the x-ray imaging device senses the transfer of the x-ray attenuating gas from the sealed object into the chamber by determining the presence of the x-ray attenuating gas present in the chamber.

21. The system of claim 18, wherein the x-ray imaging device is adjustable between the ranges of at least 1 kilovolt to 20 kilovolt anode-to-cathode voltage.

22. The system of claim 18, wherein the vacuum pump removes the ambient gas to create a pressure of less than $10^4$ Pa.

23. A system for detecting a leak in a sealed object, comprising:
   a chamber, into which the sealed object is placed;
   an x-ray attenuating gas source that creates a gas pressure within the chamber that is higher than the gas pressure within the sealed object; and
   an x-ray imaging device that senses the transfer of the x-ray attenuating gas from the chamber into the sealed object.

24. The system of claim 23, wherein the x-ray imaging device divides the object into a plurality of planar slices by way of computer-aided tomography.

25. The system of claim 23, wherein the x-ray imaging device determines that an amount of x-ray attenuating gas has entered the sealed object by detecting the gas in the sealed object.

26. The system of claim 25, wherein the x-ray imaging device determines that an amount of x-ray attenuating gas has entered the sealed object by sensing an amount of the gas remaining in the chamber.

27. The system of claim 23, wherein the x-ray attenuating gas source that creates a gas pressure within the chamber that is between $5 \times 10^4$ and $1.5 \times 10^5$ Pa.

28. A system for detecting a leak in a sealed object, comprising:
   means for enclosing a sealed object;
   means for filling the means for enclosing the sealed object with an x-ray attenuating gas; and
   means for imaging the sealed object using a device that senses the transfer of the x-ray attenuating gas between the means for enclosing the sealed object and the sealed object.

29. The system of claim 28, wherein the means for filling the means for enclosing the sealed object with an x-ray attenuating gas produces a gas pressure that is substantially higher than the gas pressure within the sealed object.

30. The system of claim 28, wherein the means for imaging the sealed object is an x-ray imaging device.

31. The system of claim 28, wherein the x-ray imaging device uses computer tomography.

32. The system of claim 28, wherein the attenuating gas is selected from the group consisting of krypton, xenon, and radon.

* * * * *

UNITED STATES PATENT AND TRADEMARK OFFICE
CERTIFICATE OF CORRECTION

| | | |
|---|---|---|
| PATENT NO. | : 7,062,012 B1 | Page 1 of 1 |
| APPLICATION NO. | : 11/009240 | |
| DATED | : June 13, 2006 | |
| INVENTOR(S) | : Kiong Chin Chng et al. | |

It is certified that error appears in the above-identified patent and that said Letters Patent is hereby corrected as shown below:

In column 2, line 54, delete "10B" and insert -- 100B --, therefor.

Signed and Sealed this

Twenty-fourth Day of March, 2009

JOHN DOLL
*Acting Director of the United States Patent and Trademark Office*